(12) United States Patent
Lopez et al.

(10) Patent No.: US 8,747,741 B2
(45) Date of Patent: *Jun. 10, 2014

(54) COSMETIC PRODUCT STERILIZATION

(71) Applicant: CL Tech, Ales (FR)

(72) Inventors: Didier Lopez, Ales (FR); Christophe Lopez, Ales (FR)

(73) Assignee: CL Tech (Societe par Actions Simplifiee), Ales (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/933,545

(22) Filed: Jul. 2, 2013

(65) Prior Publication Data

US 2013/0291487 A1 Nov. 7, 2013

Related U.S. Application Data

(63) Continuation of application No. 12/096,722, filed as application No. PCT/FR2007/051489 on Jun. 21, 2007, now Pat. No. 8,501,091.

(30) Foreign Application Priority Data

Jun. 23, 2006 (FR) .................................. 06 52617

(51) Int. Cl.
*A61L 2/00* (2006.01)

(52) U.S. Cl.
USPC ............................ 422/38; 422/308; 426/521

(58) Field of Classification Search
USPC ...................... 422/38, 307, 308; 426/521, 522
See application file for complete search history.

(56) References Cited

U.S. PATENT DOCUMENTS

| | | | |
|---|---|---|---|
| 4,994,291 A | 2/1991 | Swartzel et al. |
| 5,403,564 A | 4/1995 | Katschnig et al. |
| 5,976,592 A | 11/1999 | Polato |
| 6,551,644 B1 | 4/2003 | Allaf et al. |
| 2002/0164159 A1 | 11/2002 | De Stoutz |

FOREIGN PATENT DOCUMENTS

| | | |
|---|---|---|
| FR | 2 774 911 A1 | 8/1999 |
| GB | 1 056 681 A | 1/1967 |
| JP | 11-137644 A | 5/1999 |

OTHER PUBLICATIONS

International Search Report of PCT/FR2007/051489, date of mailing Jan. 18, 2008 (3 pages).

*Primary Examiner* — Timothy Cleveland

(74) *Attorney, Agent, or Firm* — Westreman, Hattori, Daniels & Adrian, LLP

(57) ABSTRACT

The invention relates to a method for sterilizing a cosmetic product, in which said product consists of a fluid circulating under regulated pressure in a sterilization circuit (1), according to the viscosity of said fluid. The invention also relates to the device for implementing such a method.

9 Claims, 1 Drawing Sheet

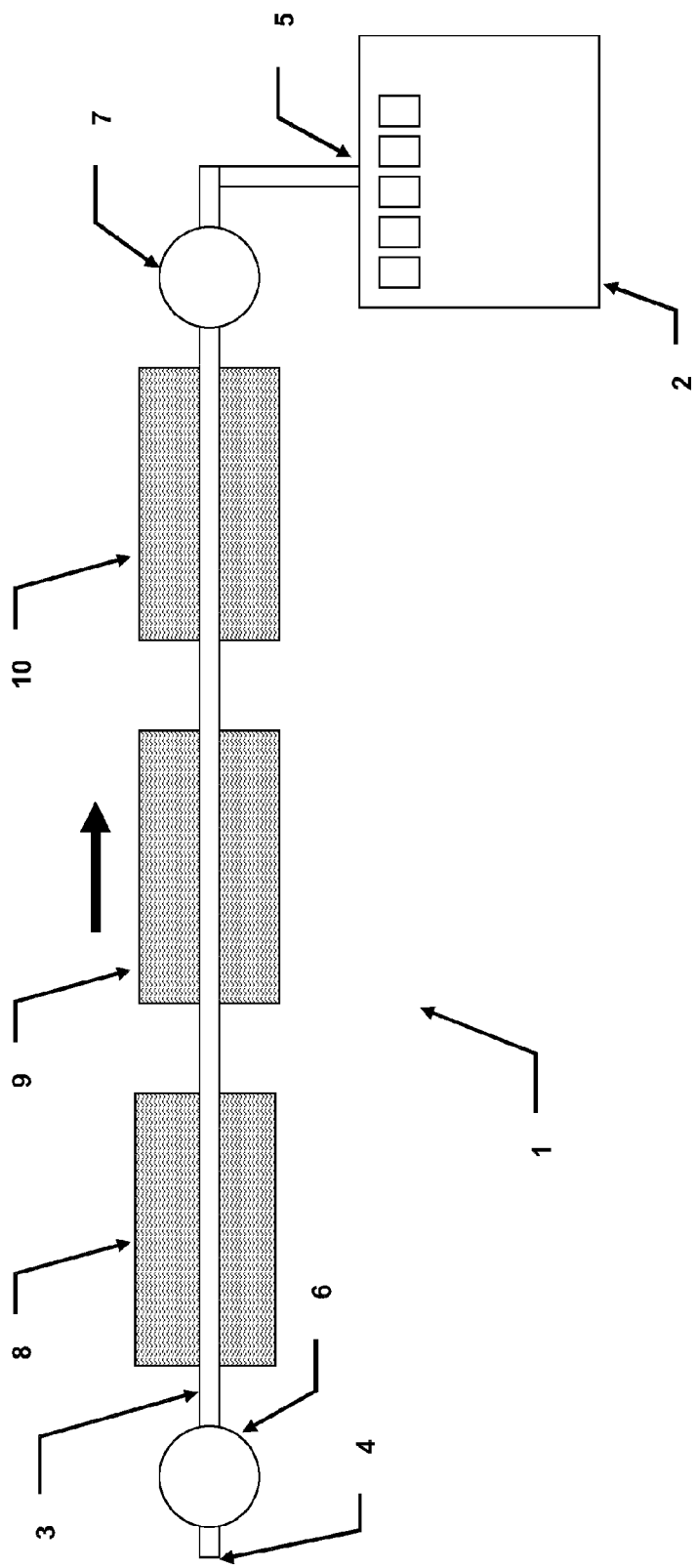

COSMETIC PRODUCT STERILIZATION

This application is a continuation of U.S. application Ser. No. 12/096,722 filed Sep. 8, 2008, which is a U.S. national stage of PCT/FR2007/51489 filed Jun. 21, 2007, whose contents are hereby incorporated by reference herein in their entirety.

BACKGROUND OF THE INVENTION (1) Field of the Invention

This invention relates to a method for sterilizing a cosmetic product, in which said product consists of a fluid circulating under pressure within a sterilization circuit, the method consisting in successively preheating said product; briefly heating said product at high temperature; immediately cooling said product; and packaging the product in a sterile atmosphere.

This invention falls within the field of cosmetology, in particular the manufacture of cosmetic products.

The invention relates more specifically to a method for sterilizing cosmetic products and a device for its implementation.

(2) Description of the Prior Art

In order to improve the preservation of a cosmetic product, in its composition are included preservatives having in particular the function of preserving the properties of said product, yet protecting it against contamination. The preservatives are classified in a list identified by authorized organizations. One group of preservatives used are parabens that prevent the growth of fungi and bacteria. However, these components have the disadvantage of being harmful to the body and are a hazard for users' health.

Producers therefore try to substitute parabens by other compounds that can be used as preservatives. However, the products used are not always present in the authorized lists and they do not provide full satisfaction.

Therefore, it was thought to sterilize the cosmetic products instead of incorporating preservatives. Several methods and devices of the state of the art, described for example in JP 60025907 and JP 10025235, consist in sterilizing, by heating, the cosmetic product in a temperature range between 50 and 80 degrees Celsius. However, the devices do not provide full satisfaction as to the longevity of the product and are complex to be implemented.

Therefore, it has been thought of sterilizing at very high temperature, in the range of 135° to 150°, still by means of circulating a fluid through a circuit traversing heating and cooling baths. Such a device is described in US 2002/164159, for sterilizing several types of products, as cosmetics, but the application of which is designed in particular for milk sterilization.

This device has disadvantages in that it is designed for the sterilization of one single product. As a matter of fact, the sterilization time in this case is adapted by increasing or diminishing the length of the circuit. Therefore, the same plant can only be dedicated to one single product, having a certain viscosity. Furthermore, the sterilization time is very long, in the range of 80 minutes, by means of circulation within a Joule-effect tubular exchanger. The high temperatures combined with this long time require high speed of product circulation, in the range of 5 meters per second.

Other solutions have been contemplated, for example in U.S. Pat. No. 5,976,592, having recourse to an electromagnetic field in order to irradiate the product and thus heat it, then cool it in a water and glycol bath at approximately 15 degrees Celsius. Such a device does not provide full satisfaction, in particular because of the complexity and of the production and utilization cost. Furthermore, one installation is dedicated to the sterilization of one and the same product having a certain viscosity.

SUMMARY OF THE INVENTION

The object of the invention is to cope with the disadvantages of the state of the art by providing a method for manufacturing a cosmetic product that does not require adding preservatives to the composition of a cosmetic product.

Furthermore, one and the same installation permits the sterilization of products having different density or viscosity. By adapting the circulation pressure of the product, this invention controls its sterilization time, i.e. the heating and the cooling.

To this end, the invention consists in sterilizing the cosmetic products by means of a quick passage at high temperature followed by an immediate cooling through a specific device.

The invention, therefore, relates to a method for sterilizing a cosmetic product, in which said product consists of a fluid circulating under regulated pressure, according to the viscosity of said fluid, within a sterilization circuit traversing baths of heated product. Such a method is characterized in that it consists in successively preheating said product in a preheating bath; in heating quickly, for about a few seconds, said product in a bath at high temperature, then cooling immediately and abruptly said product in a cold glycol bath; and in packaging the product in a sterile atmosphere.

The invention also relates to the device for implementing such a sterilization method, which device includes a sterilization circuit capable of circulating a fluid under regulated pressure successively through means for preheating said fluid in the form of a heated product bath; means for heating said fluid at high temperature in the form of a high-temperature product bath; means for cooling said fluid, in the form of a glycol bath, toward means for packaging in a sterile atmosphere.

BRIEF DESCRIPTION OF THE DRAWINGS

Other features and advantages of the invention will become clear from the following detailed description of the non-limitative embodiments of the invention, referring to the attached figure representing schematically the steps of the invention.

DETAILED DESCRIPTION OF THE PREFERRED EMBODIMENTS

This invention relates to the sterilization of a cosmetic product and consists in the sterilization at high temperature of said cosmetic product followed by its immediate cooling.

The sterilization principle of the invention is similar to the sterilization of products in the agro-alimentary field called <<UHT>>, for ultra high temperature.

UHT sterilization consists in preheating a product then bringing it to a high temperature during a short period of time before cooling it down to ambient temperature, the product thus treated being then packed up aseptically.

Therefore, this invention consists in preheating the cosmetic product, heating it briefly up to a high temperature, then cooling it.

One of the features of the invention consists in that the cosmetic product is circulating within a sterilization circuit 1. From then on, the product is no longer in contact with the outside during its sterilization and its packing, avoiding any risk of contamination after sterilization.

As a matter of fact, the packaging of the product is performed in a sterile atmosphere. This aseptic packaging area 2 can preferably include a ceiling blowing filtered air. The packaging of the product there is performed under vacuum, without any air entry, in order to avoid any contaminant.

The sterilization circuit 1 is designed capable of circulating a fluid under pressure. To this end, said circuit 1 is in the form of a sheath 3 inside which the fluid is put under pressure from an inlet 4 toward an outlet 5.

At the inlet 4, at one end of said sheath, are placed the product supply and a pump 6 permitting the putting under pressure of said circuit 1.

At the outlet 5, at the opposite end of said sheath, at the level of the means for aseptic packaging 2, are placed means for regulating the pressure 7, in particular a regulation gate.

According to one embodiment, the sterilization circuit 1 includes a coil inside which circulates the cosmetic product fluid. Said coil can preferably have an inner diameter of 5 millimeters.

Preferably, according to a particular embodiment, said circuit 1 is made of a stainless material through a sheath having a diameter of 5 to 10 mm. The coil lengths in each of the baths, mentioned hereinafter, are identical. Furthermore, the specific shape, in particular a helical shape, ensures a homogenization of heating and cooling inside the product circulating therein.

It should be noted that an essential feature of this invention therefore consists in the obligation that the cosmetic product should be in the form of a fluid. The pressure inside the circuit 1 is regulated according to its viscosity. According to the embodiment and the fluid inserted into the circuit 1, this pressure can vary from 8 to 160 bars, preferably between 80 and 120 bars. This high pressure ensures a better emulsification of the products, in particular of cosmetic products.

The sterilization circuit 1 traverses successively, but not restrictively, preheating means 8, heating means 9 and cooling means 10.

According to the preferred embodiment, said preheating 8, heating 9 and cooling 10 means are in the form of a heated product bath, the temperature of the product depending on the type of bath, heating or cooling bath.

According to the preferred embodiment of the invention, the cooling means 10 include a glycol bath at −10 degrees Celsius, the preheating means 8 include a bath at 90 degrees Celsius in order to ensure heating inside the product to at least 70° C., whereas the heating means 9 include a hot bath at 180 degrees Celsius in order to ensure heating inside the product to at least 135° C. However, temperature values of different baths can vary significantly according to the product to be sterilized.

In most cases, the bath temperature is maintained stable and only the time for the passage of the fluid inside said baths varies. As a matter of fact, the invention consists in using the movement of the product from one thermal area to another, while regulating their exposure times.

The passage in the bath at a very high temperature occurs quickly, within a period not exceeding a few seconds. In particular, the passage time in the heating means 9 can be 3 seconds.

The passage time can be regulated by varying the pressure, also according to the viscosity of the fluid traversing the circuit 1.

The successive passage from high temperature to very low temperature, preferably a negative temperature, improves sterilization and preservation of the product. As a matter of fact, even if the product itself does not pass to a negative temperature, this abrupt cooling prevents degradation of said product.

Finally, through a sterilization system similar to the method called <<UHT>>, this invention can process continuously, or without interruption, cosmetic products having different viscosities without modifying the installation.

The sterilization method according to the invention will find a particular application within the range of cosmetic products based on thermal water. As a matter of fact, the sterilization at high temperature permits to preserve the minerals and trace elements present in water. Within this range fall in particular the following products: aqueous and cleansing lotions, cleansing gels, shampoos, oil-in-water emulsions, etc.

The invention is of course not limited to the examples illustrated and described above, which can be varied and modified without however departing from the scope of the invention.

What is claimed is:

1. Method for successively sterilizing first and second fluid cosmetic products within a same sterilization circuit traversing heated product baths, wherein the first product has a first viscosity and the second product has a second viscosity different from the first viscosity, which method comprises successively:
   (i) circulating the first product in said sterilization circuit at a first regulated pressure, and
   (ii) circulating the second product in said sterilization circuit at a second regulated pressure,
   wherein each of said circulating steps comprises successively:
      preheating said product in a preheating bath;
      heating quickly said product in a bath at high temperature, then cooling immediately and abruptly said product in a cold glycol bath; and
      packaging said product in a sterile atmosphere,
   wherein the first regulated pressure is different from the second regulated pressure, so that the pressure is regulated in accordance to the viscosity of said product, and each of the first and second regulated pressures is in a range of from 8 to 160 bars,
   wherein the sterilization circuit comprises a sheath having an inner diameter from 5 to 10 millimeters, wherein the sheath includes a first section in the preheating bath, a second section in the high temperature product bath, and a third section in the glycol bath,
   and wherein each of the first and second products is circulated in the sheath at the first and second regulated pressure, respectively, during the preheating, heating and cooling of the circulating step,
   so that each of the first and second products is preheated in the preheating bath to at most 90 degrees C. and heated in the high temperature bath to at least 135 degrees C.

2. Method according to claim 1, wherein the sterilization circuit comprises means for pressurizing said product at an end of said sheath and means for regulating pressure at another end of said sheath.

3. Method according to claim 1, wherein a passage time of each of the first and second products in the high temperature bath is about 3 seconds.

4. Method according to claim 3, wherein the first, second and third sections have identical lengths.

5. Method according to claim 1, wherein each of the first and second regulated pressures is in a range from 80 to 160 bars.

6. Method according to claim 1, wherein each of the first and second regulated pressures is in a range from 80 to 120 bars.

7. Method according to claim 1, wherein the preheating bath is at a temperature that ensures heating inside the products to a temperature of from 70 degrees Celsius to 90 degrees Celsius.

8. Method according to claim 7, wherein the high temperature bath is at a temperature that ensures heating inside the products to a temperature in the range of from 135 degrees Celsius to 150 degrees Celsius.

9. Method according to claim 1, wherein the high temperature bath is at a temperature that ensures heating inside the products to a temperature in the range of from 135 degrees Celsius to 180 degrees Celsius.

* * * * *